US009173917B2

(12) United States Patent
Nagasawa et al.

(10) Patent No.: US 9,173,917 B2
(45) Date of Patent: Nov. 3, 2015

(54) METHODS FOR REDUCING OXIDATIVE STRESS IN A CELL WITH A SULFHYDRYL PROTECTED GLUTATHIONE PRODRUG

(75) Inventors: Herbert T. Nagasawa, Richfield, MN (US); Jonathan F. Cohen, Prior Lake, MN (US)

(73) Assignees: Max International, LLC, Salt Lake City, UT (US); The United States of America as represented by the Department of Veteran Affairs, Washington, DC (US)

( * ) Notice: Subject to any disclaimer, the term of this patent is extended or adjusted under 35 U.S.C. 154(b) by 0 days.

(21) Appl. No.: 13/547,430

(22) Filed: Jul. 12, 2012

(65) Prior Publication Data

US 2012/0295855 A1 Nov. 22, 2012

Related U.S. Application Data

(63) Continuation of application No. 12/190,556, filed on Aug. 12, 2008, now abandoned, which is a continuation of application No. 10/750,005, filed on Dec. 30, 2003, now abandoned.

(60) Provisional application No. 60/437,872, filed on Jan. 3, 2003.

(51) Int. Cl.
*A61K 38/06* (2006.01)
*A61P 43/00* (2006.01)

(52) U.S. Cl.
CPC .................................... *A61K 38/063* (2013.01)

(58) Field of Classification Search
None
See application file for complete search history.

(56) References Cited

U.S. PATENT DOCUMENTS

| | | | | |
|---|---|---|---|---|
| 4,710,489 | A | 12/1987 | Meister | |
| 5,382,679 | A | 1/1995 | Galzigna et al. | |
| 5,824,693 | A | 10/1998 | Goldberg et al. | |
| 6,013,663 | A * | 1/2000 | Fujita et al. | 514/440 |
| 6,030,950 | A | 2/2000 | Ohlenschlager | |
| 6,159,500 | A | 12/2000 | Dempolos et al. | |
| 6,197,749 | B1 | 3/2001 | Hamuro et al. | |
| 6,369,106 | B1 | 4/2002 | Atlas et al. | |
| 6,586,404 | B1 | 7/2003 | Dempolos et al. | |

FOREIGN PATENT DOCUMENTS

| | | |
|---|---|---|
| EP | 0494405 | 7/1992 |
| EP | 0501641 | 9/1992 |
| EP | 0572110 | 12/1993 |
| WO | 9200320 | 1/1992 |
| WO | 9829375 | 7/1998 |
| WO | 0180831 | 11/2001 |
| WO | 0180832 | 11/2001 |
| WO | 0217962 | 3/2002 |
| WO | 02090314 | 11/2002 |
| WO | 2005025570 | 3/2005 |

OTHER PUBLICATIONS

Kleinman, W. A., et al., Status of glutathione and other thiols and disulfides in human plasma, Biochemical Pharmacology, Jul. 1, 2000;60(1):19-29.
Sato, S., et al., Identification of thioether intermediates in the reductive transformation of gonyautoxins into saxitoxins by thiols, Bioorganic & Medical Chemistry Letters, Aug. 21, 2000;10(16):1787-1789.
Nagasawa, H. T., et al., Protection agains acetaminophen-induced hepatotoxicity by L-CySSME and its N-acetyl and ethyl ester derivatives, Journal of Biochemical Toxicology, 1996;11(6):289-295.
Purdie, J. W., et al., Gamma-Radiolysis of Cysteine-Cysteamine Disulfide in Aqueous solution, Canadian J. of Chemistry, 1971;49;725-730.
Fan, J., et al., Liposomal antioxidants provide prolonged protection against acute respiratory distress syndrome. Surgery 2000;128:332-338.
Prescott, L. F., et al., Intravenous N-acetylcysteine: the treatment of choice for paracetamol poisoning. Br. Med. J. 1979;2:1097-1100.
Chasseaud, L. F., Reactions with electrophiles after enzyme catalyzed deacetylation of N-acetylcysteine. Biochem. Pharmacol. 1974;23:1133-1134.
Vina, J., et al., Maintenance of glutathione content in isolated hepatocytes, Biochem. J. 1978:170:627-630.
Bessems, J.G.M., et al., Paracetamol (acetaminophen)-induced toxicity: molecular and biochemical mechanisms, analogues and protective approaches. Crit. Rev. Toxicol. 2001;31:55-138.
Williamson, J.M., et al., Intracellular cysteine delivery system that protects against toxicity by promoting glutathione synthesis. Proc. Natl. Acad. Sci. USA 1982;79:6246-6249.
Nagasawa, H.T., et al., 2-Substituted thiazolidine-4(R)-carboxylic acids as prodrugs of L-cysteine. Protection of mice against acetaminophen hepatoxicity. J. Med. Chem.I984;27;591-596.
Roberts, J. C., et al., Prodrugs of L-cysteine as protective agents against acetaminophen-induced hepatotoxicity-(Polyhydroxyalkyl)- and 2-(polyacetoxyalkyl)thiazolidine-4(i?)-carboxylic acids. J. Med. Chem. 1987;30:1891-1896.
Holleschau A.M. et al., An HPLC radiotracer method for assessing the ability of L-cysteine prodrugs to maintain glutathione levels in the cultured rat lens. Current Eye Research 1996;15:501-510.
Eriksson, B., et al., Synthesis and characterization of the L-cysteine-glutathoine mixed disulfide. Acta Chem. Scand. 1967;21:1304-1312.
Butler JDB, et al., Accumulation of cystine from glutahione-cysteine mixed disulfide in cystinotic fibroblasts: blockade by an inhibitor of D-glutamyl transpeptidase. Life Sciences 1982;31:2563-2570.
Stein A.F., et al., High-performance liquid chromaographic analysis of glutahione and its thiol and disulfide degradation products. J. Chromatog. 1986;381.259-270.

(Continued)

*Primary Examiner* — Thomas S Heard
(74) *Attorney, Agent, or Firm* — Pepper Hamilton LLP

(57) ABSTRACT

The present invention relates to compositions and methods for reducing oxidative stress in a cell, increasing glutathione levels in a cell, increasing L-cysteine levels in a cell and reducing hepatocytotoxicity by contacting a cell with a sulfhydryl protected glutathione prodrug or a sulfhydryl protected cysteine prodrug.

12 Claims, 4 Drawing Sheets

(56) References Cited

OTHER PUBLICATIONS

Meister, A., et al., Glutathione deficiency produced by inhibition of its synthesis, and its reversal; applications in research and therapy. Pharmac. Ther. 1991;51:155-194.
Anderson, M. E., GSH and GSH delivery compounds. Adv. Pharmacol. 1997;38:65-78.
White, A. C., et al., Glutathione deficiency in human disease. J. Nutr. Biochem. 1994;5:218-226.
Crankshaw, D. L., et al., Double-prodrugs of L-cysteine: differential protection against acetaminophen-induced hepatotoxicity in mice. J. Biochem. Mol. Toxicol. 2002; 16:1-10.
Anderson, M. E., et al., Glutathione monoesters. Anal. Biochem. 1989; 183:16-20.
Eriksson, S.A., et al., The reduction of the L-cysteine-glutathione mixed disulfide in rat liver. Involvement of an enzyme catalyzing thiol-disulfide interchange. FEBS Lett. 1970;7:26-28.
Fernandez-Checa, J. C., et al., Mitochondrial Glutathione depletion in alcoholic liver disease. Alcohol 1993:10:469-475.
Herzenberg, L. A., et al., GSH deficiency is associated with impaired survival in HIV disease. Proc. Nat. Acad. Sci. 1997;94:1967-1972.
Malorni, W., et al., The role of oxidative imbalance in progression to AIDS: effect of the thiol supplier jV-acetylcysteine. AIDS Res, Human Retroviruses 1998;14:1589-1596.
Martensson, J., et al., GSH ester prevents buthionine sulfoxmine-induced cataracts and lens epithelial cell damage. Proc. Nat. Acad. Sci. 1989;86:8727-8731.
Rathbun, W. B., et al., Maintenance of hepatic glutathione homeostasis and prevention of acetaminophen induced cataract in mice by L-cysteine prodrugs. Biochem. Pharmacol. 1996;51:1111-1116.
Hudson, V. M., et al., Rethinking cystic fibrosis pathology: the critical role of abnormal reduced glutathione (GSH) transport caused by CFTR mutation. Free Rad. Biol. Med. 2001 ;30:1440-1461.
Kobayashi, H., et al., The effects of D-glutamylcysteine ethyl ester, a prodrug of GSH, on ischemia-reperfusion-induced liver injury in rats. Transplantation 1992;54:414-418.
Leaf, C. D., et al., Development of a novel glutathione repleting agent, L-2-oxothJazolidine-4-carboxylic acid (Procysteine). Exp. Opin. Invest. Drugs 1994;3:1293-1302.
Jonas et al., "Cystine accumulation and loss in normal, heterozygous, and cystinotic fibroblasts," Proc Natl Acad Sci USA (1982) 79(14):4442-4445.
Badaloo et al., "Cysteine supplementation improves the erythrocyte glutathione synthesis rate in children with severe edematous malnutrition," Am J Clin Nutr (2002) 76(3):646-652.
Shirota et al., "Acetaminophen-induced suppression of hepatic AdoMet synthetase activity is attenuated by prodrugs of L-cysteine," Toxicology Letters (2002) 1-8.

* cited by examiner

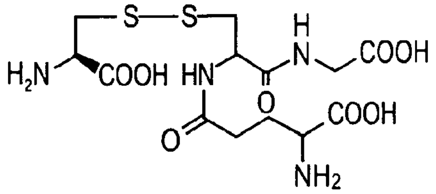

L-CySSG

(W.A. Kleinman and J.R. Richie, Biochem. Pharmocol. 60, 19-29, 2000)

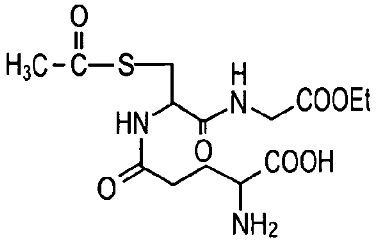

S-Acetylglutathione ethyl ester (S-Ac-GSH-OE)

[Lauro Galzigna PCT/EP9/01154 (WO 92/00320)]

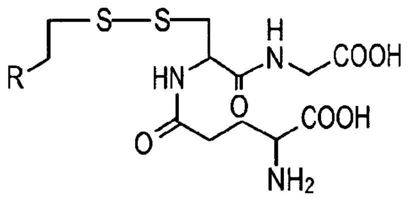

GSSMA ($R = NH_2$)

(D.A. Kleine, E. Strauss, W. Guo, B. Noszal and D.L. Rabenstein, J. Org. Chem. 57, 123-127, 1992)

GSSME (R = OH)

S. Sato, R. Sakai and M Kodama, Biloorg. Med. Chem. Lett. 10, 1787-1789, 2000

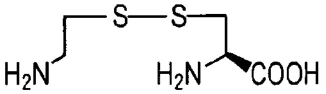

CySSMA

(J.W. Purdue, Can. J. Chem. 49, 725-730, 1971)

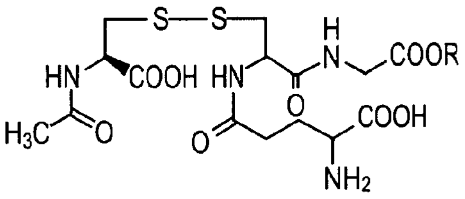

R = Et; i-Pr; n-Bu

Derivatives of CySSG

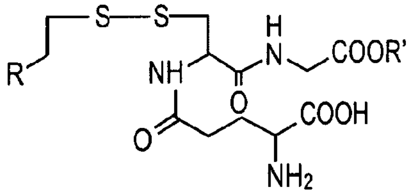

R= $H_2N$-; $(CH_3)_2N$-: $(C_2H_5)_2N$-; 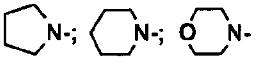

R' = $C_1$-$C_{18}$ alkyl, cyctoelkyl (mono-, bi-, tri-), aralkyl, aryl

Derivatives of CySSMA

FIG. 2

METHODS FOR REDUCING OXIDATIVE STRESS IN A CELL WITH A SULFHYDRYL PROTECTED GLUTATHIONE PRODRUG

CROSS-REFERENCE TO RELATED APPLICATIONS

This application is a continuation of U.S. application Ser. No. 12/190,556, filed Aug. 12, 2008, which is a continuation of U.S. application Ser. No. 10/750,005 filed Dec. 30, 2003, which claims the benefit of the filing date of U.S. Provisional Application Ser. No. 60/437,872, filed Jan. 3, 2003, each of which is hereby incorporated by reference in its entirety.

The invention described herein was made with U.S. Government support under a Merit Review funded proposal entitled, "Application of Medical Chemistry to Alcoholic Liver disease" awarded by the Department of Veterans Affairs to Herbert Tsukasa Nagasawa, Ph.D. The invention was also made in part with funding under Grant Number DA07234 awarded by the National Institutes of Health. The United States Government has certain rights in the invention.

Throughout this application various publications are referenced. The disclosures of these publications in their entireties are hereby incorporated by reference into this application in order to more fully describe the state of the art to which this invention pertains. The invention has been described with reference to various specific and preferred embodiments and techniques. However, it should be understood that many variations and modifications may be made while remaining within the spirit and scope of the invention.

BACKGROUND OF THE INVENTION

Drug-induced hepatotoxicity is a major cause of new drug withdrawal from the market. It also limits further development of promising therapeutic agents even prior to clinical trials. Over-the-counter drugs are not exempt from hepatotoxic liability; for example, acetaminophen (ACP), a widely used (and misused) analgesic/antipyretic agent, when taken acutely in large doses, or chronically in greater than recommended dosages, can lead to liver and kidney damage. While individual pharmacogenetic profiles of hepatic cytochrome P-450 isozyme patterns, when correlated with chemical structures of the drugs and their possible metabolic activation pathways, hold promise as means to preclude susceptible subjects from drug exposure, the concept of therapeutic intervention or prevention methods have not yet attracted much attention, despite the fact that the standard clinical option for protecting the liver from ACP overdoses is to administer intravenous N-acetyl-L-cysteine (NAC) within 8 hours of the overdose (1). NAC, following deacetylation in the liver (2), provides L-cysteine, the sulfhydryl amino acid required for the rate-limiting first step in the biosynthesis of glutathione (GSH) (3). GSH is the body's natural defense against endogenously generated reactive oxidant species as well as reactive species such as NAPQI produced in the metabolism of ACP (4).

Experimentally, the administration of high doses of ACP to mice produces fulminant hepatic necrosis, manifested by quantum elevations in serum transaminase levels and histological evidence of centrilobular necrosis leading eventually to death. Post-administration of NAC, a prodrug of L-cysteine, or other cysteine prodrugs that have been sulfhydryl-modified, effectively protect mice against this ACP-induced hepatotoxicity (5, 6, 7).

Using a $^{14}$C-glycine/HPLC assay method to determine the extent of incorporation of the cysteinyl moiety of the cysteine prodrugs into GSH in rat lens (8), a radioactive peak near GSH was discovered which appeared to be produced metabolically. This substance was tentatively identified as the mixed disulfide of L-cysteine with GSH, viz., L-cysteine-GSH disulfide (CySSG). CySSG is produced endogenously via a thiol-disulfide exchange reaction between GSH and L-cystine (9), and possibly, the reaction of L-cysteine with GSSG (the oxidized form of GSH). CySSG, postulated to be a storage form of L-cysteine (10), has been detected in small quantities (relative to GSH) in liver and kidney samples from rats, but is present in comparable amounts as GSH, cysteine and cystine in rat and human plasma (11, 12).

Except for the monoesters (on the glycyl moiety) and the diethyl ester of GSH, prodrugs of GSH (13) have not been systematically investigated as protective agents against xenobiotic-induced hepatotoxicity.

Currently, there is a need for agents to treat cellular oxidative stress and to increase glutathione and L-cysteine levels in a cell. Such agents would also be useful to treat hepatotoxicity associated with the administration of other therapeutic agents.

SUMMARY OF THE INVENTION

Sulfhydryl protected glutathione prodrugs (FIG. 2) such as L-CySSG, GSSMA, GSSME and acetylglutathione ethyl ester (S-Ac-GSH-OEt) as well as sufhydryl protected cysteine prodrugs such as CySSMA (FIG. 2) or CySSME (see infra) are precursors to glutathione and/or cysteine. In a cell, the prodrugs are cleaved to release glutathione and/or cysteine molecules.

Sulfhydryl protected glutathione prodrugs and sufhydryl protected cysteine prodrugs were assayed for their protective effect against ACP-induced hepatotoxicity using a recently developed mouse model (14,15).

L-CySSG was found to be a highly effective liver protective agent in this model (FIG. 1), even surpassing the activities of glutathione monoethyl ester (GSH-OEt) (16) and the cysteine prodrug, L-CySSME [S-(2-hydroxymethylmercapto)-L-cysteine] (14). These results indicate that L-CySSG may have general therapeutic application in treating cellular oxidative stress.

Additionally, compounds such as GSSMA, GSSME, CySSMA and S-acetylglutathione ethyl ester (S-Ac-GSH-OEt) are useful for treating oxidative stress in the mouse model (FIGS. 1, 3 and 4).

Accordingly, the invention provides compositions and methods for regulating cellular oxidative stress, hepatotoxicity, glutathione and/or L-cysteine levels in a cell comprising contacting a cell with an effective amount of a sulfhydryl protected glutathione prodrug such as L-CySSG, GSSMA, GSSME and S-Ac-GSH-OEt, derivatives thereof or pharmaceutically acceptable salts thereof, or a sufhydryl protected cysteine prodrug, derivatives thereof or pharmaceutically acceptable salts thereof.

The invention also provides a pharmaceutical composition comprising a sulfhydryl protected glutathione prodrug such as L-CySSG, GSSMA, GSSME and S-Ac-GSH-OEt, derivatives thereof or pharmaceutically acceptable salts thereof, for regulating oxidative stress, hepatotoxicity, glutathione and/or L-cysteine levels in a cell. Additionally, the invention provides a pharmaceutical composition comprising a sulfhydryl protected cysteine prodrug such as CySSMA (L-CySSMA, D-CySSMA or DL-CySSMA), derivatives thereof or pharmaceutically acceptable salts thereof, for regulating oxidative stress, hepatotoxicity, glutathione and/or L-cysteine levels in a cell

BRIEF DESCRIPTION OF THE FIGURES

FIG. 2. Diagrams showing the structures of sulfhydryl protected glutathione and cysteine prodrugs (with references to their preparation) and the structures of the derivatives of CySSG and GSSMA.

DETAILED DESCRIPTION

Figure 1:
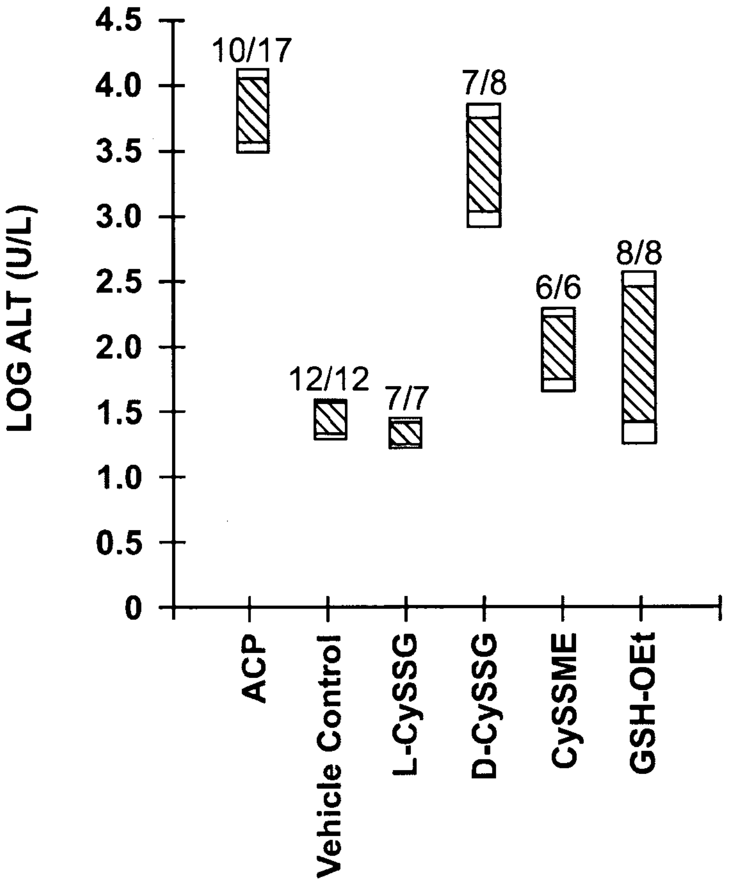
FIG. 1. A graph showing protection from ACP-induced hepatotoxicity in mice by CySSG using protocol 4'B (for CySSME only, the protocol was 3'B).

The present invention provides compositions and methods for regulating (e.g., reducing) oxidative stress in a cell by contacting a cell with a sulfhydryl protected glutathione prodrug or a sulfydryl protected cysteine prodrug. In one embodiment, the oxidative stress can be caused by decreased or depleted cellular levels of glutathione. The sulfhydryl protected glutathione prodrug or the sulfhydryl protected cysteine prodrug can regulate (e.g., increase) the glutathione and/or cysteine levels in the cell, thereby reducing the oxidative stress in the cell.

Examples of sulfhydryl protected glutathione prodrugs include but are not limited to L-CySSG, GSSMA, GSSME, acetylglutathione ethyl ester (S-Ac-GSH-OEt) and derivatives thereof.

As used herein, the terms sulfhydryl protected glutathione prodrugs or sulfhydryl protected cysteine prodrugs encompasses any racemic, optically-active, polymorphic, or stereoisomeric form, or mixtures thereof it being well known in the art how to prepare optically active forms (for example, by resolution of the racemic form by recrystallization techniques, by synthesis from optically-active starting materials, by chiral synthesis, or by chromatographic separation using a chiral stationary phase). Reference to D-CySSMA refers to the enantiomer having the same absolute configuration as D-Cysteine, while reference to L-CySSMA refers to the enantiomer having the same absolute configuration as L-Cysteine. Contrary to the lack of significant activity found for D-CySSG (discussed herein), D-CySSMA is useful for preventing cellular oxidative stress.

Reference to L-CySSG refers to the enantiomer having the same absolute configuration as L-Cysteine in the cysteine portion of the molecule. However it will be appreciated that a racemic or scalemic mixture including L-CySSG can be used or administered to provide L-CySSG according to the invention. In one embodiment, L-CySSG is used or administered as a mixture that is optically enriched in the enantiomer having the same absolute configuration as L-Cysteine.

Preferably, L-CySSG is administered as a mixture having an enantiomeric excess of at least about 90%, 95%, or 98% of the enantiomer having the same absolute configuration as L-Cysteine. More preferably, L-CySSG is administered as a mixture having an enantiomeric excess of at least about 99% of the enantiomer having the same absolute configuration as L-Cysteine.

In cases where prodrugs are sufficiently basic or acidic to form stable nontoxic acid or base salts, administration of the prodrugs as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The present invention also provides compositions and methods for regulating (e.g., increase) glutathione and/or cysteine levels in a cell by contacting a cell with a sulfhydryl protected glutathione prodrug or a sulthydryl protected cysteine prodrug so as to increase the glutathione and/or cysteine levels in the cell. For example, after administration of a sulfhydryl protected glutathione or cysteine prodrug to a subject, the prodrug is cleaved and releases glutathione and/or L-cysteine which can then contact the cells of the subject.

The present invention provides compositions and methods for regulating (e.g., reducing) hepatotoxicity in a subject by reducing oxidative stress in a cell in the subject. In one embodiment, the hepatotoxicity is reduced by administering to the subject a sulfhydryl protected glutathione prodrug or a sulfhydryl protected cysteine prodrug. The sulfhydryl protected glutathione prodrug or the sulfhydryl protected cysteine prodrug can increase the glutathione and/or cysteine levels in the cell, thereby reducing the hepatotoxicity in the subject.

The present invention also provides compositions and methods for prolonging drug therapy by decreasing the toxicity of the drug comprising administering to a subject a sulfhydryl protected glutathione prodrug or a sulfhydryl protected cysteine prodrug. Additionally, the present invention provides methods for increasing a therapeutic dosage of a drug by decreasing the toxicity of the drug comprising administering to a subject a sulfhydryl protected glutathione prodrug or a sulfhydryl protected cysteine prodrug.

The present invention also provides compositions and methods for regulating oxidative stress, hepatocytotoxicity, glutathione levels and L-cysteine levels in a cell by contacting said cell with a sulfhydryl protected glutathione prodrug or a sulfydryl protected cysteine prodrug.

Oxidative stress can be caused by a number of agents, including, but not limited to, a toxic substance, a pathogen, ultraviolet light, aging, physical injury and/or genetic disease. In one embodiment, the toxic substance is a drug, alcohol, metal ion, ultraviolet light or radiation. In another embodiment, the drug is acetominophen, an aminoglycoside antibiotic or a chemotherapeutic drug. In another embodiment, the pathogen is HIV or anthrax spores.

In one embodiment, reducing oxidative stress reduces injury caused by aging, Alzheimer's disease, Parkinson's disease, infection (e.g., viral infection such as with HIV, herpes virus, rabies virus, hepatitis virus or bacterial infection, e.g., by *Bacillus anthracis*, the cause of anthrax), cardiovascular disease (e.g., congestive heart failure, vasoconstriction caused by poor utilization of nitric oxide, atherosclerosis), genetic disease (e.g., Cystic Fibrosis), physical injury (e.g., ischemic reperfusion injury), ophthalmic disease (e.g., cataracts, macular degeneration), cancer (e.g., breast cancer, melanoma), inflammation (e.g., regional enteritis, ulcerative colitis (Crohn's disease)), neuropathy (e.g., sensorineural hearing loss), acute respiratory distress syndrome (ARDS), emphysema, exposure to a toxic substance (e.g., alcohol, acetaminophen, naphthalene, aminoglycoside antibiotics (e.g., gentamicin, kanamycin), chemotherapeutic drugs, metal ions, catecholamines), exposure to a free radicals, exposure to ultraviolet light (e.g., cataracts), exposure to radiation and/or decreased levels of glutathione. The sulfhydryl protected glutathione prodrugs or sulfhydryl protected cysteine prodrugs of the invention are also useful to treat other conditions associated with oxidative stress, including those described in U.S. Pat. Nos. 6,423,687, 6,204,248, and 6,159,500, as well as sensorineural hearing loss (SNHL) (U.S. Pat. No. 6,177,434).

As shown in FIG. 1, the plasma alanine aminotransferase (ALT) levels of ACP-treated mice, when a sulfhydryl protected glutathione prodrug such as L-CySSG was implemented as the hepatoprotective agent, were not different from that of vehicle control animals at the 99% confidence level. In contrast, a sulfhydryl protected glutathione prodrug such as D-CySSG, prepared from D-cysteine in the same manner as L-CySSG (12), was not hepatoprotective, with ALT levels statistically similar to that for ACP alone (without drug treatment) at the 95% confidence level. The relative hepatoprotective properties of a sulfhydryl protected glutathione prodrug such as L-CySSG, a sulfhydryl protected cysteine prodrug such as CySSME and a glutathione prodrug without sulfhydryl protection such as GSH-OEt (16) can be compared readily by visual inspection of the data of FIG. 1.

The remarkable efficacy of L-CySSG in protecting mice against ACP toxicity, contrasted to the lack of hepatoprotection by D-CySSG, suggests that GSH is being released enzymatically from L-CySSG. This could be the consequence of a direct enzymatic reduction of the disulfide bond, or from the GSH-dependent thiol-disulfide exchange reaction with CySSG catalyzed by liver glutathione reductase (GR) (17), viz.,

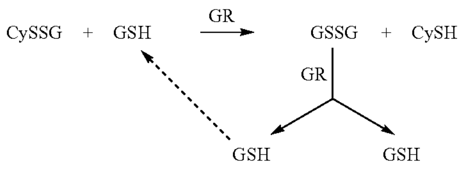

In either case, the result would be the overall reduction of the disulfide bond leading to the net intracellular release of GSH as well as L-cysteine. Thus, a sulfhydryl protected glutathione prodrug such as CySSG provides not only GSH itself, but also L-cysteine which is the key amino acid for de novo GSH biosynthesis.

In an embodiment, an important structural feature of a sulfhydryl protected glutathione prodrug or a sulfhydryl protected cysteine prodrug is that the reactive sulfhydryl groups of these prodrugs are protected by a disulfide linkage. For example in CySSG, both reactive sulfhydryl groups of the GSH and cysteine moieties are masked in a disulfide linkage. Unlike GSH or its carboxy esters with free —SH groups that are subject to oxidation, a sulfhydryl protected glutathione prodrug such as CySSG is stable (9, 17), and may be used as a prophylactic agent to prevent or abort hepatotoxicity by co-administration or co-formulation with potentially hepatotoxic drugs. Also, because the sulfhydryl protected glutathione prodrug CySSG is a ubiquitous endogenous product of cells and, now, a demonstrated prodrug of GSH, it may be beneficial as a dietary supplement either alone or admixed with other known nutrients to maintain GSH homeostasis and cellular antioxidant levels. In one embodiment, sulfhydryl protected glutathione prodrugs such as L-CySSG, GSSMA, GSSME, S-Ac-GSH-OEt and derivatives thereof, are precursors to glutathione and/or cysteine. In another embodiment, sufhydryl protected cysteine prodrugs such as CySSMA (FIG. 2) and derivatives thereof, are precursors to cysteine and/or glutathione.

In accordance with the invention, sulfhydryl protected glutathione prodrugs or sulfhydryl protected cysteine prodrugs such as CySSG, as well GSSMA, GSSME, CySSMA and S-Ac-GSH-OEt are useful for treating cellular oxidative stress caused by GSH depletion known to manifest in alcoholic liver disease, AIDS, cataracts, cystic fibrosis, ischemic reperfusion injury, and acute respiratory distress syndrome (ARDS), among others indications.

In an embodiment of the invention, the sulfhydryl protected glutathione prodrug L-CySSG is administered to a subject suffering from a drug or substance induced toxicity (e.g., acetaminophen, alcohol). In another embodiment of the invention, the sulfhydryl protected glutathione prodrug L-CySSG is administered to a subject prior to or during induction of the drug or substance induced toxicity, whereby administration of L-CySSG reduces or prevents the drug or substance induced toxicity.

In another embodiment of the invention, the sulfhydryl protected glutathione prodrug L-CySSG is administered to a subject, thereby reducing or preventing hepatotoxicity.

In another embodiment of the invention, the sulfhydryl protected glutathione prodrug L-CySSG is administered to a subject, thereby reducing or preventing cirrhosis or necrosis of the liver induced by a toxic agent e.g., alcohol, hepatotoxic drug.

As used herein, "oxidative stress" refers to the deleterious effects on a cell or system induced by metabolic processes of a cell or system or by an agent to a cell or system. Causes of oxidative stress can include, but is not limited to the following agents or causes: depletion of glutathione, a toxic substance e.g., a drug, metal or alcohol, a pathogen, ultraviolet light, radiation, free radicals, aging, physical injury and/or genetic disease.

As used herein, "hepatoxicity" refers to the capacity or ability of an agent (e.g., toxic substance, free radical, pathogen), exposure (e.g., radiation) or other cause (e.g., genetic disease, physical injury) to cause injury to the liver.

As used herein, a "prodrug" refers to a compound, which is converted by a metabolic process within a body, organ or cell, thereby releasing a pharmacologically active form.

As used herein, the term "treatment" or "treating" refers to any treatment of a pathologic condition in a subject e.g., a human, and includes: preventing the pathologic condition from occurring, e.g. prophylactic treatment in a subject; inhibiting the development of the pathologic condition; relieving or causing regression of the pathologic condition; and relieving the conditions mediated by the pathologic condition. The subject includes, but is not limited to a human, monkey, dog, cat, cow, sheep, horse, rabbit, mouse, or a rat.

The sulfhydryl protected glutathione prodrug or a sulfhydryl protected cysteine prodrug of the invention can be formulated as a pharmaceutical composition with an acceptable carrier which is an ion exchanger, alumina, aluminum stearate, lecithin, serum protein such as human serum albumin, buffer substance, glycine, sorbic acid, potassium sorbate, partial glyceride mixture of saturated vegetable fatty acids, phosphate buffered saline solution, water, emulsion, salt or electrolyte, colloidal silica, magnesium trisilicate, polyvinyl pyrrolidone, cellulose-based substance, polyethylene glycol, sterile solution, tablet, excipient, sucrose, glucose, maltose, flavor and color additive, lipid composition and/or polymeric composition.

The prodrug of the invention can be formulated as pharmaceutical compositions and administered to a subject, such as a human subject in a variety of forms adapted to the chosen route of administration, i.e., aerosol, orally or parenterally, by intravenous, intramuscular, topical or subcutaneous routes implantable pump, continuous infusion and/or oral administration.

The prodrug of the invention can be formulated as a pharmaceutical composition further comprising an agent that causes cellular oxidative stress, where the agent is acetominophen, alcohol, aminoglycoside antibiotics (e.g. gentamicin, kanamycin) or a chemotherapeutic drug.

Thus, the prodrug of the invention may be systemically administered, e.g., in an aerosol or orally, in combination with a pharmaceutically acceptable vehicle such as an inert diluent or an assimilable edible carrier. They may be enclosed in hard or soft shell gelatin capsules or as liposomes, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Administration of the compositions of the invention can be made before, during or after exposure to an agent that causes cellular oxidative stress (e.g., acetaminophen). A composition of the invention can be administered alone or in combination with other composition(s) of the invention. Further, administration of the composition of the invention can be sequential or concurrent with administration of other pharmaceutical composition(s).

Useful dosages of the compounds of can be determined by comparing their in vitro activity, and in vivo activity in animal models. Methods for the extrapolation of effective dosages in mice, and other animals, to humans are known to the art; for example, see U.S. Pat. No. 4,938,949. The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In one embodiment of the invention, a sulfhydryl protected glutathione prodrug, L-CySSG, is administered to a subject in an effective amount comprising e.g. 0.2 to 2.5 mmol/kg body weight of the subject. In another embodiment, the sulfhydryl protected glutathione prodrug is administered to a subject in an effective amount of 50-500 milligrams per day.

The sulfhydryl protected glutathione or cysteine compounds CySSG, GSSMA, GSSME, CySSMA and S-Ac-GSH-OEt can be prepared from readily available starting materials using procedures that are generally known in the field of synthetic chemistry, for example see: W. A. Kleinman and J. R. Richie, *Biochem. Pharmacol.,* 2000, 60, 19-29; T. W. Hart, M. S. Vine and N. R. Walden, Tetrahedron Lett., 1985, 26:3879-3882; S. Sato, R. Sakai and M. Kodama, *Bioorg. Med. Chem. Lett.* 2000, 10, 1787-1789; D. A. Keine et al., *J. Org. Chem.,* 1992, 57, 123-127; J. W. Purdue, *Con. J. Chem.,* 1971, 49, 725-730; and WO 92/00320.

The following example is presented to illustrate the present invention and to assist one of ordinary skill in making and using the same. The example is not intended in any way to otherwise limit the scope of the invention.

Example 1

Methods

Sulfhydryl protected glutathione prodrugs, sulfhydryl protected cysteine prodrugs and derivatives thereof are shown in FIG. 2.

Male Swiss-Webster mice weighing 24-34 g were administered ACP [360 mg (or 2.45 mmol)/kg, i.p.].

In protocol 4'B, a priming dose of the prodrug (1.25 mmole/kg, i.p.) was administered 60 min prior to ACP followed by a subsequent dose (2.50 mmol/kg) 30 min post-ACP.

In protocol 3'B, the pre- and post-ACP doses were reversed.

In protocol 1, a single dose of drug was administered 30 min post-ACP.

Figure 3:
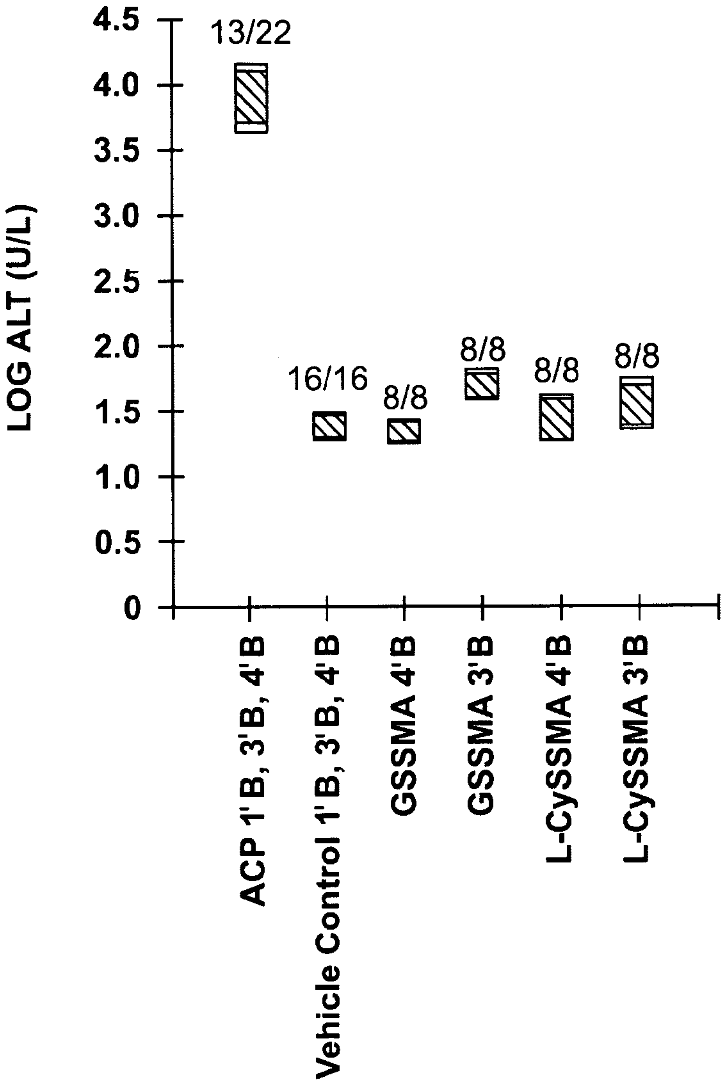
FIG. 3. A graph showing protection from ACP-induced hepatotoxicity in mice by GSSMA and L-CySSMA under four different protocols. The data for ACP and vehicle controls from different protocols are combined.
Figure 4:
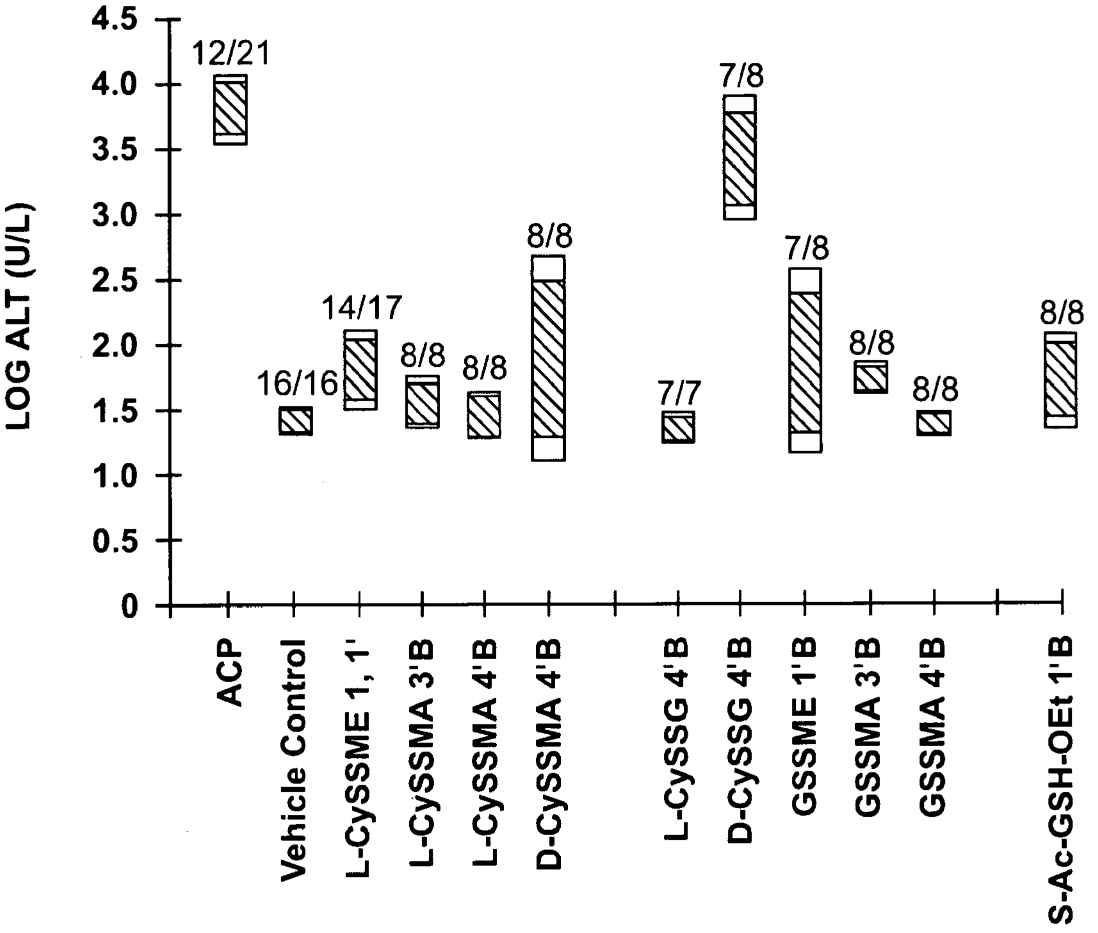
FIG. 4. A graph showing a comparison of the protective effect of sulfhydryl protected cysteine and glutathione prodrugs from ACP-induced hepatotoxicity in mice.

Protocol 1' is identical to 3'B except that the pH of the injection solution was not adjusted. In the B series, the pH of the injection solution was adjusted to neutrality with dilute, aqueous NaOH or HCl The animals (survival rates as shown in FIGS. 1, 3 and 4) were sacrificed 24 hrs post-ACP for measurement of plasma ALT levels. The mice were considered to be fully protected when the 99% (hatched) or 95% (unhatched) confidence levels of the log transformed ALT levels for the group overlapped with the corresponding confidence levels of the vehicle control animals (14).

Results

As shown in FIG. 1, the plasma alanine aminotransferase (ALT) levels of ACP-treated mice, when the sulfhydryl protected glutathione prodrug L-CySSG was implemented as the hepatoprotective agent, were similar to that of vehicle control animals at the 99% confidence level. In contrast, the sulfhydryl protected glutathione prodrug D-CySSG, prepared from D-cysteine in the same manner as L-CySSG (12), showed ALT levels comparable to that for ACP alone without prodrug treatment. FIG. 1 also shows the relative hepatoprotective properties of L-CySSG (a sulfhydryl protected glutathione prodrug), CySSME (a sulfhydryl protected cysteine prodrug) and GSH-OEt (a glutathione prodrug without sulfhydryl protection)(16).

As shown in FIG. 3, the relative effects of sulfhydryl protected glutathione prodrug GSSMA and sulfhydryl protected cysteine prodrug L-CySSMA were assayed under varying experimental protocols. The prodrugs induced comparable protection against ACP treatment in mice with protocol 4'B when compared to the vehicle control. The prodrugs when used in protocol 3'B also induced very effective protection in ACP-treated mice.

FIG. 4, shows the relative hepatoprotective properties of various sulfhydryl protected glutathione or cysteine prodrugs in ACP-treated mice. L-forms of the prodrugs showed more protection than the D-forms.

CITED DOCUMENTS

1. Prescott L F, Illingworth R N, Critchley J A J H, Stewart M J, Adam R D, Proudfoot A T. Intravenous N-acetylcysteine: the treatment of choice for paracetamol poisoning. Br. Med. J. 1979; 2:1097-1100.
2. Chasseaud L F. Reactions with electrophiles after enzyme catalyzed deacetylation of N-acetylcysteine. Biochem. Pharmacol. 1974; 23:1133-1134.
3. Vina J, Reginald H, Krebs H A. Maintenance of glutathione content in isolated hepatocytes. Biochem. J. 1978; 170: 627-630.
4. Bessems J G M, Vermeulen N P E. Paracetamol (acetaminophen)-induced toxicity: molecular and biochemical mechanisms, analogues and protective approaches. Crit. Rev. Toxicol. 2001; 31:55-138.
5. Williamson J M, Boettcher B, Meister A. Intracellular cysteine delivery system that protects against toxicity by promoting glutathione synthesis. Proc. Natl. Acad. Sci. USA 1982; 79:6246-6249.
6. Nagasawa H T, Goon D J W, Muldoon W P, Zera R T. 2-Substituted thiazolidine-4(R)-carboxylic acids as prodrugs of L-cysteine. Protection of mice against acetaminophen hepatoxicity. J. Med. Chem. 1984; 27:591-596.
7. Roberts J C, Nagasawa H T, Zera R T, Fricke R F, Goon D J W. Prodrugs of L-cysteine as protective agents against acetaminophen-induced hepatotoxicity. 2-(Polyhydroxyalkyl)- and 2-(polyacetoxyalkyl)thiazolidine-4(R)-carboxylic acids. J. Med. Chem. 1987; 30:1891-1896.
8. Holleschau A M, Rathbun W B, Nagasawa H T. An HPLC radiotracer method for assessing the ability of L-cysteine prodrugs to maintain glutathione levels in the cultured rat lens. Current Eye Research 1996; 15:501-510.
9. Eriksson B, Eriksson, S A. Synthesis and characterization of the L-cysteine-glutathione mixed disulfide. Acta Chem. Scand. 1967; 21:1304-1312.
10. Butler J D B, Spielberg S P. Accumulation of cystine from glutathione-cysteine mixed disulfide in cystinotic fibroblasts; blockade by an inhibitor of □-glutamyl transpeptidase. Life Sciences 1982; 31:2563-2570.
11. Stein A F, Dills R L, Klaassen C D. High-performance liquid chromatogaphic analysis of glutathione and its thiol and disulfide degradation products. J. Chromatog. 1986; 381:259-270.
12. Kleinman W A, Richie Jr. J P. Status of glutathione and other thiols and disulfides in human plasma. Biochem. Pharmacol. 2000; 60:19-29.
13. Anderson M E. GSH and GSH delivery compounds. Adv. Pharmacol. 1997; 38:65-78.
14. Nagasawa H T, Shoeman D W, Cohen J F, Rathbun W B. Protection against acetaminophen-induced hepatotoxicity by L-CySSME and its N-acetyl and ethyl ester derivatives. J. Biochem. Toxicol. 1996; 11:289-295.
15. Crankshaw D L, Berkeley L I, Cohen J F, Shirota F N, Nagasawa H T. Double-prodrugs of L-cysteine: differential protection against acetaminophen-induced hepatotoxicity n mice. J. Biochem. Mol. Toxicol. 2002; 16:1-10.
16. Anderson M E, Meister A. Glutathione monoesters. Anal. Biochem. 1989; 183:16-20.
17. Eriksson S A, Mannervik B. The reduction of the L-cysteine-glutathione mixed disulfide in rat liver. Involvement of an enzyme catalyzing thiol-disulfide interchange. FEBS Lett. 1970; 7:26-28.
18. Fernandez-Checa J C, Hirano T, Tsukamoto H, Kaplowitz N. Mitochondrial GSH depletion in alcoholic liver disease. Alcohol 1993; 10:469-475.
19. Herzenberg L A, De Rosa S C, Dubs J G, Roederer M, Anderson M T, Ela S W, Deresinski S C. GSH deficiency is associated with impaired survival in HIV disease. Proc. Nat. Acad. Sci. 1997; 94:1967-1972.
20. Malorni W, Rivabene R, Lucia B M, Ferrara R, Mazzone A M, Cauda R, Paganelli R. The role of oxidative imbalance in progression to AIDS: effect of the thiol supplier N-acetylcysteine. AIDS Res. Human Retroviruses 1998; 14:1589-1596.
21. Martensson J, Steinherz R, Jain A, Meister A. GSH ester prevents buthionine sulfoximine-induced cataracts and lens epithelial cell damage. Proc. Nat. Acad. Sci. 1989; 86:8727-8731.

22. Rathbun W B, Killen C E, Holleschau A M, Nagasawa H T. Maintenance of hepatic glutathione homeostasis and prevention of acetaminophen induced cataract in mice by L-cysteine prodrugs. Biochem. Pharmacol. 1996; 51:1111-1116.

23. Hudson V M. Rethinking cystic fibrosis pathology: the critical role of abnormal reduced glutathione (GSH) transport caused by CFTR mutation. Free Rad. Biol. Med. 2001; 30:1440-1461.

24. Kobayashi H, Kurokawa T, Kitahara S, Nonami T, Harada A, Nakao A, Sugiyama S, Ozawa T, Takagi H. The effects of □-glutamylcysteine ethyl ester, a prodrug of GSH, on ischemia-reperfusion-induced liver injury in rats. Transplantation 1992; 54:414-418.

25. Leaf C D, Pace G W. Development of a novel glutathione repleting agent, L-2-oxothiazolidine-4-carboxylic acid (Procysteine). Exp. Opin. Invest. Drugs 1994; 3:1293-1302.

26. Fan J, Shek P N, Suntres Z E, Li Y H, Oreopoulos G D, Rotstein O D. Liposomal antioxidants provide prolonged protection against acute respiratory distress syndrome. Surgery 2000; 128:332-338.

27. Meister A. Glutathione deficiency produced by inhibition of its synthesis, and its reversal; applications in research and therapy. Pharmac. Ther. 1991; 51:155-194.

28. White A C, Thannickal V J, Fanburg B L. Glutathione deficiency in human disease. J. Nutr. Biochem. 1994; 5:218-226.

What is claimed is:

1. A method for reducing oxidative stress in a cell comprising administering L-CySSG to a subject, wherein L-CySSG is cleaved in the subject and releases cysteine and glutathione in the subject to reduce oxidative stress in the cell.

2. The method of claim 1, wherein the cell has decreased or depleted cellular levels of glutathione.

3. The method of claim 1, wherein the oxidative stress is caused by a toxic substance, a pathogen, ultraviolet light, physical injury or genetic disease.

4. The method of claim 3, wherein the toxic substance is a drug, alcohol, metal ion, ultraviolet light or radiation.

5. The method of claim 4, wherein the drug is acetaminophen, aminoglycoside antibiotic or a chemotherapeutic drug.

6. The method of claim 3, wherein the pathogen is HIV or anthrax spores.

7. The method of claim 1, wherein reducing oxidative stress reduces an injury caused by an infection, cardiovascular disease, genetic disease, physical injury, ophthalmic disease, cancer, inflammation, neuropathy, acute respiratory distress syndrome (ARDS), exposure to a toxic substance, exposure to ultraviolet light, exposure to radiation and/or decreased levels of glutathione.

8. The method of 1, wherein L-CySSG is administered via aerosol, intravenous, intramuscular, subcutaneous, implantable pump, continuous infusion and/or oral administration.

9. The method of claim 1, wherein the subject is selected from the group consisting of human, monkey, dog, cat, cow, sheep, horse, rabbit, mouse, and rat.

10. The method of claim 1, wherein the subject is human.

11. The method of claim 1, wherein L-CySSG is administered to the subject in an amount of 0.2 to 2.5 mmol/kg body weight of the subject.

12. The method of claim 1, wherein L-CySSG is administered to the subject in an amount of 50-500 milligrams per day.

* * * * *